(12) United States Patent  
Cully et al.

(10) Patent No.: US 8,721,819 B2  
(45) Date of Patent: May 13, 2014

(54) METHODS FOR AN EXPANDABLE COVERED STENT WITH WIDE RANGE OF WRINKLE-FREE DEPLOYED DIAMETERS

(71) Applicant: W. L. Gore & Associates, Inc., Newark, DE (US)

(72) Inventors: Edward H. Cully, Flagstaff, AZ (US); Michael J. Vonesh, Flagstaff, AZ (US)

(73) Assignee: W. L. Gore & Asociates, Inc., Newark, DE (US)

( * ) Notice: Subject to any disclaimer, the term of this patent is extended or adjusted under 35 U.S.C. 154(b) by 0 days.

(21) Appl. No.: 13/770,207

(22) Filed: Feb. 19, 2013

(65) Prior Publication Data

US 2013/0160943 A1     Jun. 27, 2013

Related U.S. Application Data

(62) Division of application No. 11/408,474, filed on Apr. 21, 2006, now Pat. No. 8,425,584.

(51) Int. Cl.
*A61F 2/06* (2013.01)

(52) U.S. Cl.
USPC ............. 156/80; 156/293; 156/294; 29/505; 29/507; 29/508; 623/1; 623/1.11; 623/1.12; 623/1.13; 623/1.15; 623/1.44

(58) Field of Classification Search
CPC ........................................................ A61F 2/07
USPC .............. 156/293, 294, 80; 29/505, 507, 508; 623/1, 1.11, 1.12, 1.13, 1.44, 1.15
See application file for complete search history.

(56) References Cited

U.S. PATENT DOCUMENTS

| | | | |
|---|---|---|---|
| 4,739,762 | A | 4/1988 | Palmaz |
| 5,534,287 | A | 7/1996 | Lukic |
| 5,653,747 | A | 8/1997 | Dereume |
| 5,735,892 | A | 4/1998 | Myers et al. |
| 5,800,522 | A | 9/1998 | Campbell et al. |

(Continued)

FOREIGN PATENT DOCUMENTS

| | | |
|---|---|---|
| EP | 1 586 286 | 10/2005 |
| WO | 9712562 | 4/1997 |
| WO | 9938455 | 8/1999 |
| WO | 0033770 | 6/2000 |

OTHER PUBLICATIONS

International Search Report and Written Opinion for PCT/US2007/009253 mailed Sep. 4, 2007, corresponding to U.S. Appl. No. 11/408,474 now patent No. 8,425,584.

*Primary Examiner* — Jeff Aftergut
*Assistant Examiner* — Jaeyun Lee
(74) *Attorney, Agent, or Firm* — Paul J. Fordenbacher

(57) ABSTRACT

An improved stent-graft device is provided that delivers a smooth flow surface over a range of operative expanded diameters by applying a unique cover material to the stent through a technique that allows the cover to become wrinkle-free prior to reaching fully deployed diameter. The unique cover material then allows the device to continue to expand to a fully deployed diameter while maintaining a smooth and coherent flow surface throughout this additional expansion. Employed with a self-expanding device, when the device is unconstrained from a compacted diameter it will self-expand up to a fully deployed diameter with the graft being substantially wrinkle-free over diameters ranging from about 30-50% to 100% of the fully deployed diameter.

19 Claims, 7 Drawing Sheets

(56) References Cited

U.S. PATENT DOCUMENTS

| | | |
|---|---|---|
| 5,843,164 A | 12/1998 | Frantzen et al. |
| 5,873,906 A | 2/1999 | Lau et al. |
| 6,015,431 A | 1/2000 | Thornton et al. |
| 6,156,064 A | 12/2000 | Chouinard |
| 6,193,745 B1 | 2/2001 | Fogarty et al. |
| 6,254,627 B1 | 7/2001 | Freidberg |
| 6,336,937 B1 | 1/2002 | Vonesh et al. |
| 6,488,701 B1 | 12/2002 | Nolting et al. |
| 6,923,827 B2 | 8/2005 | Campbell et al. |
| 2001/0053929 A1 | 12/2001 | Vonesh et al. |
| 2002/0045931 A1 | 4/2002 | Sogard et al. |
| 2002/0178570 A1 | 12/2002 | Sogard et al. |
| 2003/0082324 A1 | 5/2003 | Sogard et al. |
| 2003/0130721 A1 | 7/2003 | Martin et al. |
| 2004/0024448 A1 | 2/2004 | Chang et al. |
| 2004/0088042 A1 | 5/2004 | Kim et al. |
| 2004/0181274 A1 | 9/2004 | Brown et al. |
| 2004/0265475 A1 | 12/2004 | Hossainy et al. |
| 2005/0075715 A1 | 4/2005 | Borges et al. |
| 2006/0165754 A1 | 7/2006 | Ranade |
| 2007/0050017 A1* | 3/2007 | Sims et al. .................. 623/1.44 |

\* cited by examiner

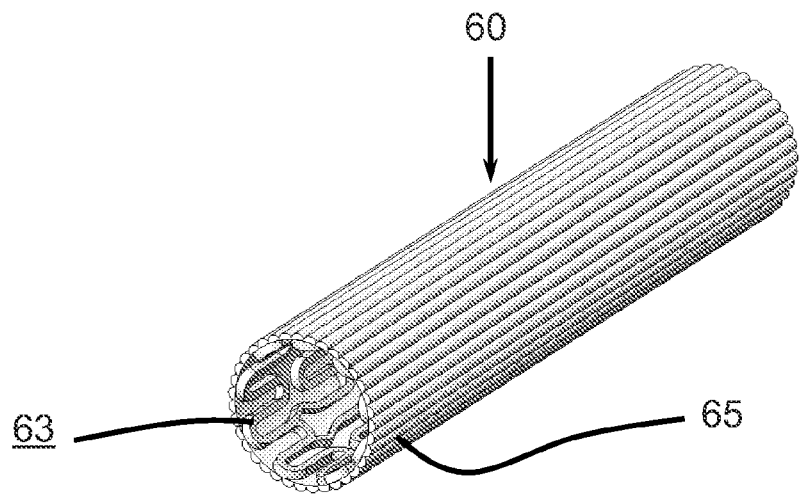
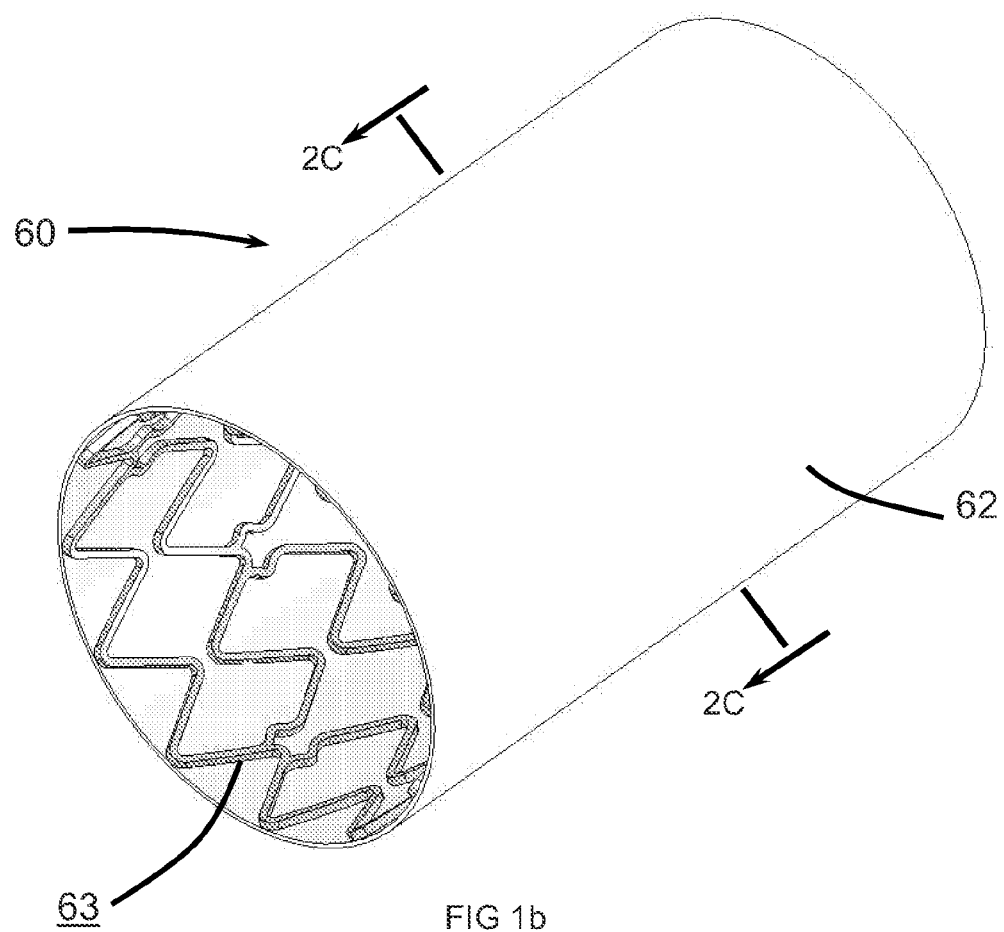
FIG 1b

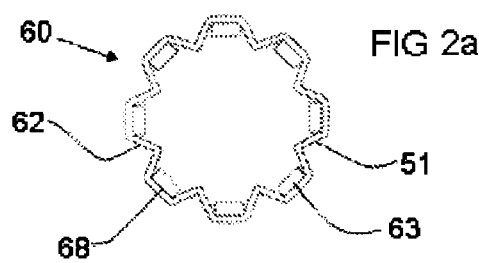
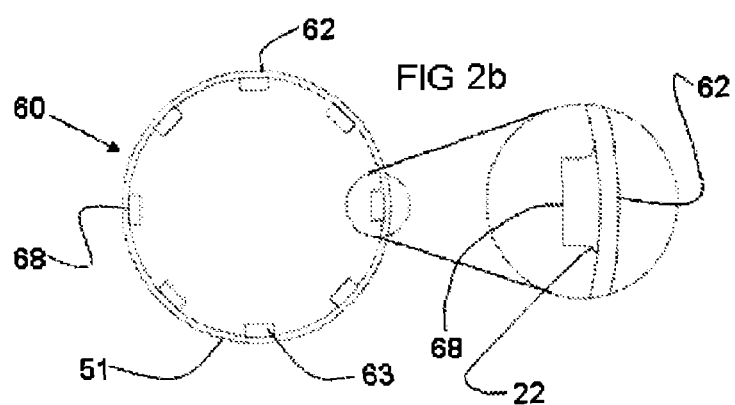
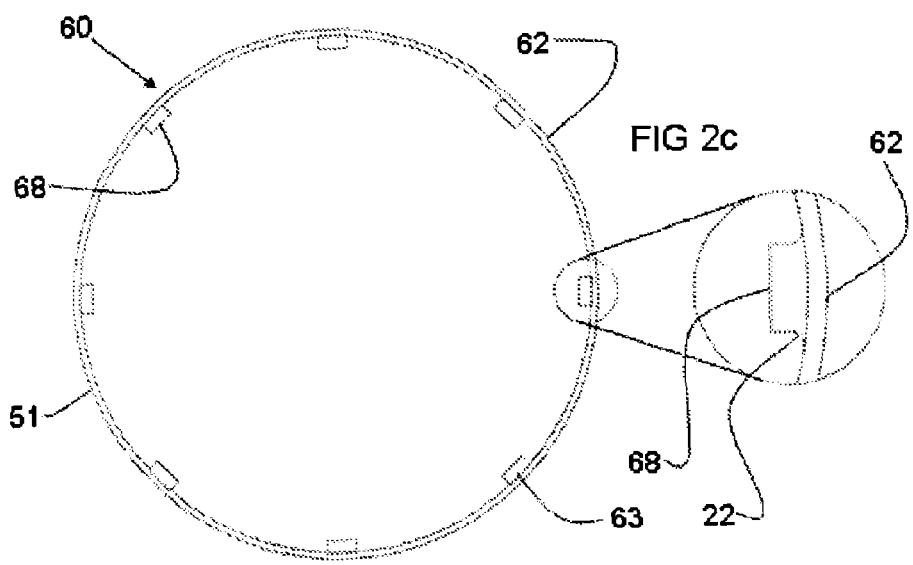

METHODS FOR AN EXPANDABLE COVERED STENT WITH WIDE RANGE OF WRINKLE-FREE DEPLOYED DIAMETERS

CROSS-REFERENCE TO RELATED APPLICATIONS

This application is a divisional of U.S. patent application Ser. No. 11/408,474 filed on Apr. 21, 2006, which is incorporated by reference herein in its entirety.

FIELD

The present invention relates to covered stents for use in various medical procedures.

BACKGROUND

The following terms used herein are defined as follows:

The term "stent" means a frame structure containing openings through its wall, typically cylindrical in shape, intended for implantation into the body. A stent may be self-expanding and/or expanded using applied forces.

As used herein, the terms "covered stent" and "stent-graft" are used interchangeably to mean a stent with a cover on at least a portion of its length. The cover can be on the outer surface, the inner surface, on both surfaces of the stent, or the stent may be embedded within the cover itself. The cover may be porous or non-porous and permeable or non-permeable. Active or inactive agents or fillers can be attached to or incorporated into the cover.

Referring to FIG. 4a, as used in this application, the term "wrinkle" 65a, 65b means a fold in a stent cover 62 that has a larger peak to valley height 64 than a thickness 66 of an adjacent stent strut 68. In the illustrated instance where the cover is mounted within the stent, a wrinkle 65a in a cover 62 on the outer surface of a covered stent 60 may be identified where the cover extends beyond the inner surface of the stent struts 68. A wrinkle 65b can also extend radially inward.

Referring to FIG. 4b, a wrinkle 65a in a cover on the inner surface of a covered stent 60 can extend radially outward. Such an outward-extending wrinkle may be identified where the cover 62 extends beyond the outer surface of the stent struts 68 as shown in FIG. 4b. A wrinkle 65b can also extend radially inward as shown in FIG. 4b Wrinkles can be observed with unaided vision or they can be observed and measured under magnification, such as optical microscopy. "Wrinkle-free" means a stent covering that is substantially free of "wrinkles."

As used herein, the term "expand" has two distinct meanings. When used in the context of describing stents, it refers to the increase in diameter of those devices. When used in the context of ePTFE material, it refers to the stretching (i.e., expansion) process used to render PTFE material stronger and porous.

As used herein, the term "self-expanding" means the attribute of a device that describes that it expands outwardly, such as in a general radial direction, upon removal of a constraining means, thereby increasing in diameter without the aid of an external force. That is, self-expanding devices inherently increase in diameter once a constraining mechanism is removed. Constraining means include, but are not limited to, tubes from which the stent or covered stent device is removed, such as by pushing. Alternatively, a constraining tube or sheath may be disrupted to free the device or the constraining means can be unraveled should it be constructed of a fiber or fibers. External forces, as provided by balloon catheters for example, may be used prior to expansion to help initiate an expansion process, during expansion to facilitate expansion, and/or after stent or covered stent deployment to further expand or otherwise help fully deploy and seat the device.

As used herein, the term "fully deployed" refers to the state of a self-expanding stent after which the constraining means has been removed and the stent, at about 37° C. over the course of 30 seconds, has expanded under its own means without any restriction. A portion or portions of a self-expanding stent may be fully deployed and the remainder of the stent may be not fully deployed.

The phrase, "operating diametric range" refers to the diametric size range over which the stent or stent-graft will be used and typically refers to the inner diameter of the device. Devices are frequently implanted in vessel diameters smaller than that corresponding to the device fully deployed state. This operating range may be the labeled size(s) that appear in the product literature or on the product package or it can encompass a wider range, depending on the use of the device.

As used herein, the term "porous" describes a material that contains small or microscopic openings, or pores. Without limitation, "porous" is inclusive of materials that possess pores that are observable under microscopic examination. "Non-porous" refers to materials that are substantially free of pores. The term "permeable" describes a material through which fluids (liquid and/or gas) can pass. "Impermeable" describes materials that block the passage of fluids. It should be appreciated that a material may be non-porous yet still be permeable to certain substances.

Stents and covered stents have a long history in the treatment of trauma-related injuries and disease, especially in the treatment of vascular disease. Stents can provide a dimensionally stable conduit for blood flow. Stents prevent vessel recoil subsequent to balloon dilatation thereby maintaining maximal blood flow. Covered stents can provide the additional benefits of preventing blood leakage through the wall of the device and inhibiting, if not preventing, tissue growth through the stent into the lumen of the device. Such growth through the interstices of the stent may obviate the intended benefits of the stenting procedure.

In the treatment of carotid arteries and the neurovasculature, coverings trap plaque particles and other potential emboli against the vessel wall thereby preventing them from entering the blood stream and possibly causing a stroke. Coverings on stents are also highly desirable for the treatment of aneurismal vascular disease. The covers may further act as useful substrates for adding fillers or other bioactive agents (such as anticoagulant drugs, antibiotics, growth inhibiting agents, and the like) to enhance device performance.

The stent covers may extend along a portion or portions or along the entire length of the stent. Generally, stent covers should be biocompatible and robust. They can be subjected to cyclic stresses about a non-zero mean pressure. Consequently, it is desirable for them to be fatigue and creep resistant in order to resist the long-term effects of blood pressure. It is also desirable that stent covers be wear-resistant and abrasion-resistant. These attributes are balanced with a desire to provide as thin a cover as possible in order to achieve as small a delivery profile as possible. Covers compromise the flow cross-section of the devices, thereby narrowing the blood flow area of the device, which increases the resistance to flow. While increased flow area is desirable, durability can be critical to the long-term performance of covered stents. Design choice, therefore, may favor the stronger, hence thicker, covering. Thick covers, however, are more resistant to distension than otherwise identical thinner covers.

Some balloon-expandable stent covers are wrinkle-free over the operating range of the stents because the extreme pressures of the balloons can distend the thick, strong covers that are placed onto the stent at a less than a fully deployed stent diameter. Even the thinnest covers in the prior art such as those made of ePTFE (e.g., those taught in U.S. Pat. No. 6,923,827 to Campbell et al., and U.S. Pat. No. 5,800,522 to Campbell et al.), however, may be too unyielding to be distended by the radial forces exerted by even the most robust self-expanding stents.

Non-elastic and non-deformable self-expanding stent covers are, therefore, generally attached in a wrinkle-free state to the stent when the stent is fully deployed. When such covered stents are at any outer diameter smaller than the fully deployed outer diameter, the cover is necessarily wrinkled. These wrinkles, unfortunately, can serve as sites for flow disruption, clot initiation, infection, and other problems. The presence of wrinkles may be especially deleterious at the inlet to covered stents. The gap between the wrinkled leading edge of the cover and the host vessel wall can be a site for thrombus accumulation and proliferation. The adverse consequences of wrinkles are particularly significant in small diameter vessels which are prone to fail due to thrombosis, and even more significant in the small vessels that provide blood to the brain.

The use of thin, strong materials is known for implantable devices (e.g., those taught in U.S. Pat. No. 5,735,892 to Myers et al.). Extremely thin films of expanded PTFE (ePTFE) have been taught to cover both self-expanding and balloon expandable stents. Typically these films are oriented during the construction of the devices to impart strength in the circumferential direction of the device. Consequently, the expanding forces of the self-expanding stents may be far too low to distend these materials. In fact, such devices are generally designed to withstand high pressures. These coverings, like those of other coverings in the art, are wrinkle-free only when the devices are fully deployed.

Thin, extruded but not expanded fluoropolymer tubes have been used to cover self-expanding and balloon-expandable stents (e.g., U.S. Patent Application 2003/0082324 A1 to Sogard). These seamless extruded tube covers are applied to self-expanding stents in the fully deployed state of the stents. The stent coverings, therefore, possess wrinkles upon crushing the device to a diameter smaller than the fully deployed diameter.

Expanded PTFE material has been used to cover stents that are self-expanding up to a given diameter, then use the assistance of a balloon catheter or other expansion force to achieve the desired clinical implantation diameter (e.g., U.S. Pat. No. 6,336,937 to Vonesh et al). Such covers are wrinkled in the range of diameters up to the diameter at which the stent expands on its own. Beyond that diameter, the covers may be relatively wrinkle-free, however, the stent may no longer be freely self-expanding.

Another type of covered stent previously disclosed (e.g., U.S. Patent Application 2002/0178570 A1 to Sogard) is constructed with two polymeric liners laminated together yet not adhered to the stent. In the absence of bonding a liner to the stent, both an inner and outer liner are necessary and they need to be bonded together at the stent openings in order to construct a coherent stent-graft. This construction provides a relatively smooth liner on one side of the stent. The outer liner follows the geometry of the stent strut and is bonded to the inner liner. As such, according to the definition of a "wrinkle" as provided herein, the outer liner is wrinkled. Expanded PTFE liners of self-expanding covered stents made with shape memory alloys were taught to be laminated together at elevated temperatures, as high as 250° C. (and below 327° C.), while not exceeding a stent temperature which might reset the shape memory state of the alloy. In the absence of bonding the liners to the stent struts, gaps are formed between the liners. Such gaps may become filled with biological materials that compromise the blood flow area and, therefore, may restrict blood flow.

Without the addition of other materials, expanded PTFE materials must be heated well above 200° C. in order the heat bond them together. Given that these stent-graft devices are intended to self-expand at body temperature, the temperature at which the alloy may reset is necessarily close to body temperature. This thermal requirement obviates the possibility of heat bonding the liner to the stent at around a 250° C. temperature. Furthermore, the size of the covered stent that can be constructed in this manner is limited by the physics of heat conduction. That is, a 250° C. heat source must be at a suitable distance from the stent during the lamination process. The liners are laminated with the stent at a diameter less than deployed diameter, hence the size of the openings of the stent are smaller than if the liners were laminated at a larger stent diameter. Consequently, small diameter covered stents cannot be made in accordance with these teachings, nor can the liners be bonded to the stent.

U.S. Pat. No. 6,156,064 to Chouinard teaches use of dip coating to apply polymers to self-expanding stents. Stents and stent-grafts are dipped into polymer-solvent solutions to form a film on the stent followed by spray coating and applying a polymeric film to the tube. Stent-grafts comprising at least three layers (i.e., stent, graft, and membrane) are taught to be constructed in this manner.

Stents have also been covered with a continuous layer of elastic material. As taught in U.S. Pat. No. 5,534,287 to Lukic, a covering may be applied to a stent by radially contracting the stent, then placing it inside a tube with a coating on its inner surface. The stent is allowed to expand, thereby bringing it in contact with the coating on the tube. The surface of contact between the stent and the tube is then vulcanized or similarly bonded. No teaching is provided concerning the diameter of the tube relative to the fully deployed stent diameter. The patent specifically teaches in one embodiment the application of the coating on a stent in the expanded condition. The inventor does not teach how to eliminate or even reduce wrinkles in the stent cover. In fact, the patent teaches how to increase the thickness of the coating, a process that would only increase the occurrence of wrinkling. The patent teaches away from the use of a non-elastic material to cover the stent, and specifically teaches away from the use of a "Teflon®" (i.e., PTFE) tube.

U.S. Patent Application 2004/0024448 A1 to Chang et al teaches covered stents with elastomeric materials including PAVE-TFE. Self-expanding stent-grafts made with this material, like those made of other materials in the art, are not wrinkle-free over the operating range of the devices. These coverings of self-expanding stents are typically applied to the stent in the fully-deployed state. Consequently, wrinkles are formed when the stent-graft is crushed to any significant degree.

SUMMARY

The present invention is an improved expandable implantable stent-graft device that provides a smooth flow surface over a range of operative expanded diameters. This is accomplished by applying a unique cover material to the stent through a unique technique that allows the cover to become wrinkle-free prior to reaching fully deployed diameter. The unique cover material then allows the device to continue to expand to a fully deployed diameter while maintaining a smooth and coherent flow surface throughout this additional expansion.

In one embodiment the present invention comprises a diametrically self-expanding stent-graft device having a graft covering attached to at least a portion of the stent. The device is adapted to be constrained into a compacted diameter for insertion into a body conduit, which will produce wrinkles along its graft surface. However, when the device is unconstrained from the compacted diameter it will self-expand up to a fully deployed diameter with the graft being substantially wrinkle-free over diameters ranging from 50% to 100% of the fully deployed diameter.

Further improvements in the present invention may include providing a fluoropolymer graft component, such as an ePTFE, in the form of either a coherent continuous tube or a film tube. The graft and stent may be combined together through a variety of means, including using heat bonding or adhesive, such as FEP or PMVE-TFE.

By modifying the materials and/or the construction techniques, the range of wrinkle-free expansions can be increased to about 30%-100% or even wider ranges.

BRIEF DESCRIPTION OF THE DRAWINGS

FIG. 1a is a three-quarter isometric view of one embodiment of a covered stent of the present invention in the constrained state, having the cover mounted on the outside of the stent;

FIG. 1b is a three-quarter isometric view of the embodiment of a covered stent of the present invention of FIG. 1a in the fully deployed state;

FIG. 2a is a transverse cross-section view of the embodiment of a covered stent of the present invention deployed to 30% of the fully deployed outer diameter of the device;

FIG. 2b is a transverse cross-section view of the embodiment of a covered stent of the present invention deployed to 50% of the fully deployed outer diameter of the device with the smooth gradual transition of the adhesive-stent cover interface shown in detail in an enlarged sectional view;

FIG. 2c is a transverse cross-section view of the embodiment of a covered stent of the present invention taken along line 2c-2c of FIG. 1b, deployed to 100% of the fully deployed outer diameter of the device with the smooth gradual transition of the adhesive-stent cover interface shown in detail in an enlarged sectional view;

DETAILED DESCRIPTION

Figure 3A:
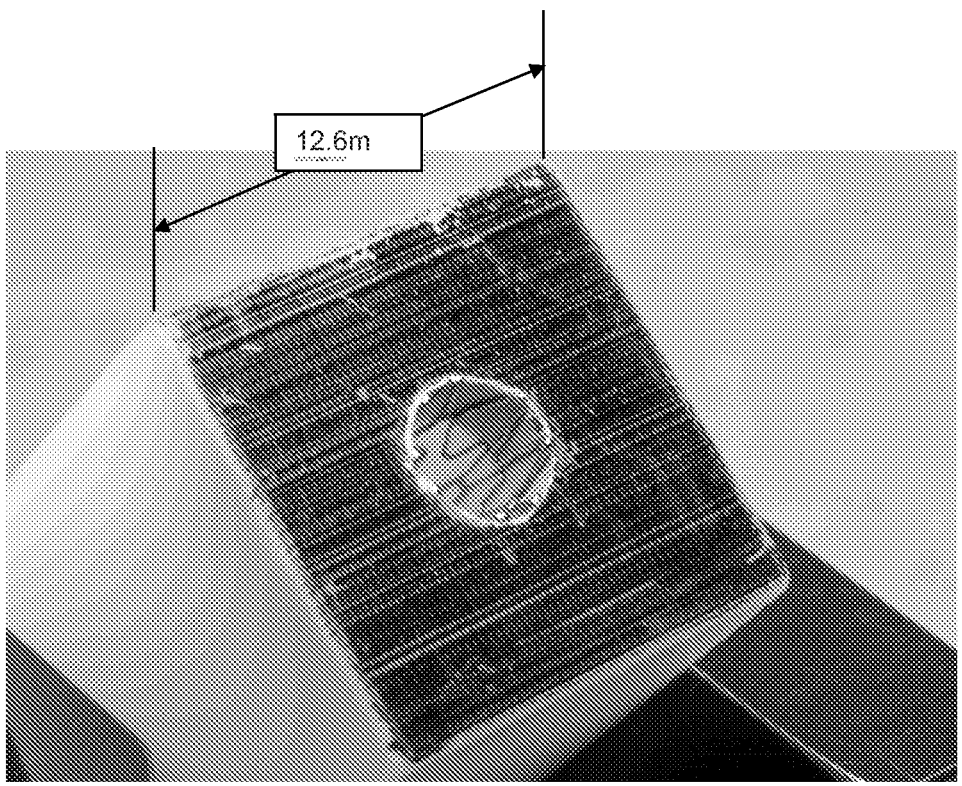
FIG. 3a is a photomicrograph showing the inside of a covered stent of the present invention that is constrained in a partially deployed state of about 50% of the fully deployed outer diameter of the device.
Figure 3B:
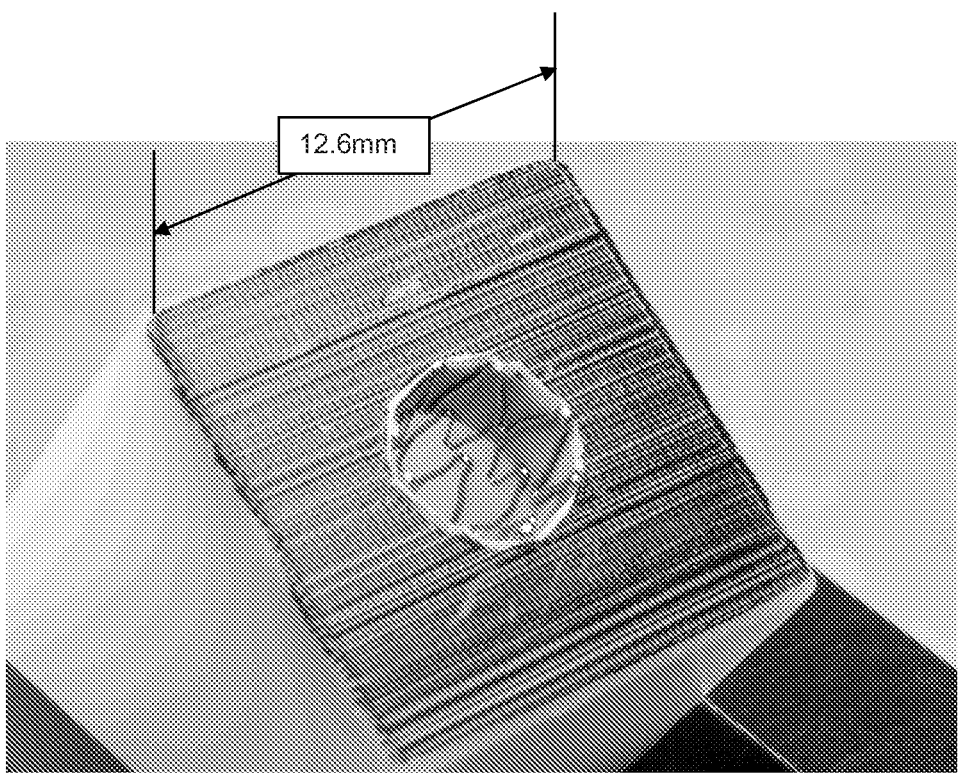
FIG. 3b is a photomicrograph showing the inside of a covered stent of the present invention that is constrained in a partially deployed state of about 60% of the fully deployed outer diameter of the device.
Figure 3C:
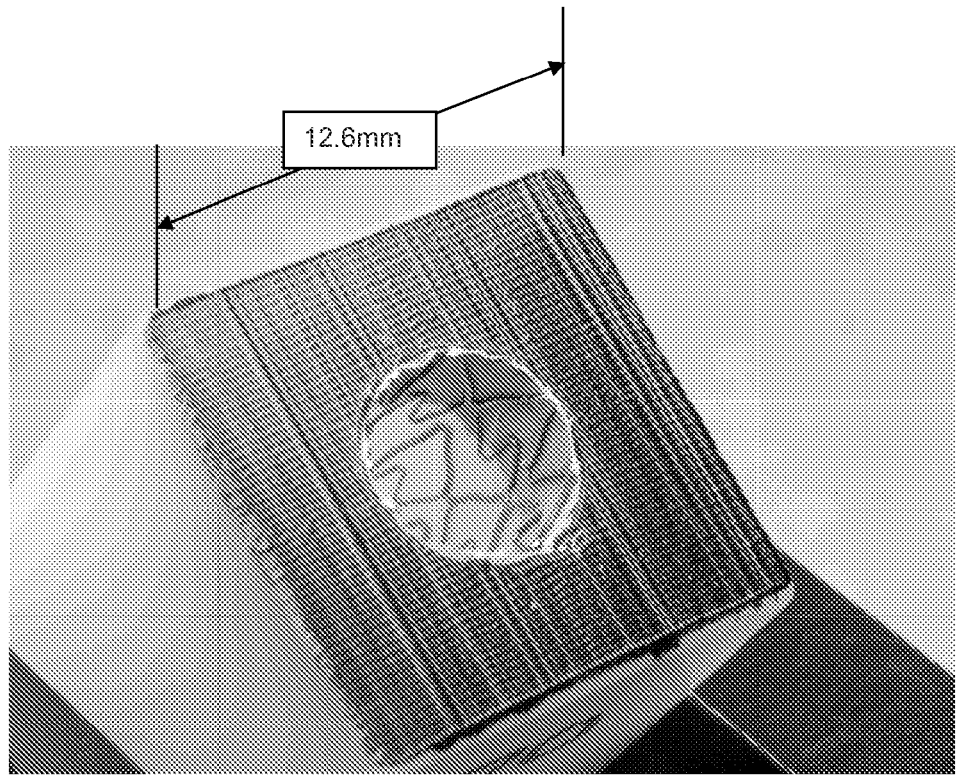
FIG. 3c is a photomicrograph showing the inside of a covered stent of the present invention that is constrained in a partially deployed state of about 70% of the fully deployed outer diameter of the device.
Figure 3D:
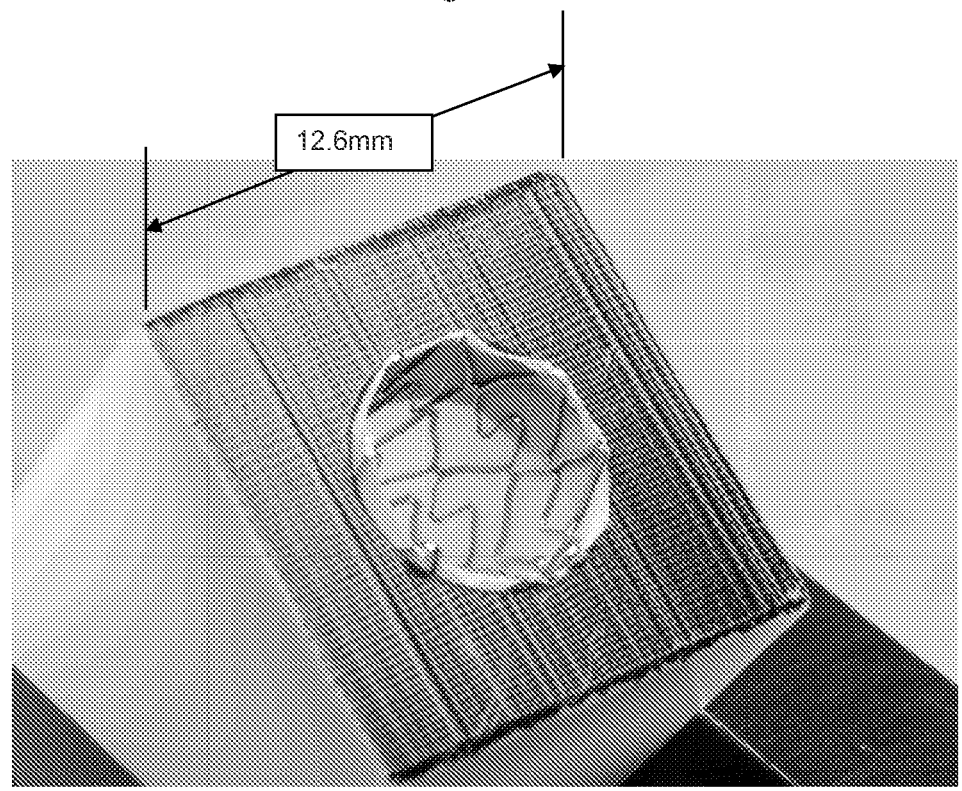
FIG. 3d is a photomicrograph showing the inside of a covered stent of the present invention that is constrained in a partially deployed state of about 80% of the fully deployed outer diameter of the device.
Figure 3E:
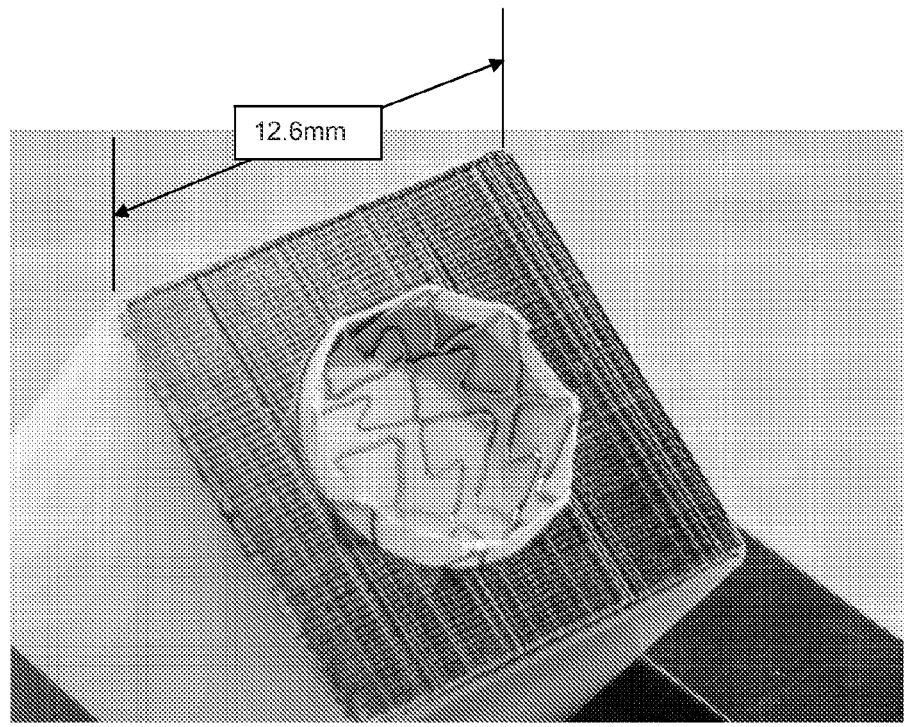
FIG. 3e is a photomicrograph showing the inside of a covered stent of the present invention that is constrained in a partially deployed state of about 90% of the fully deployed outer diameter of the device.
Figure 3F:
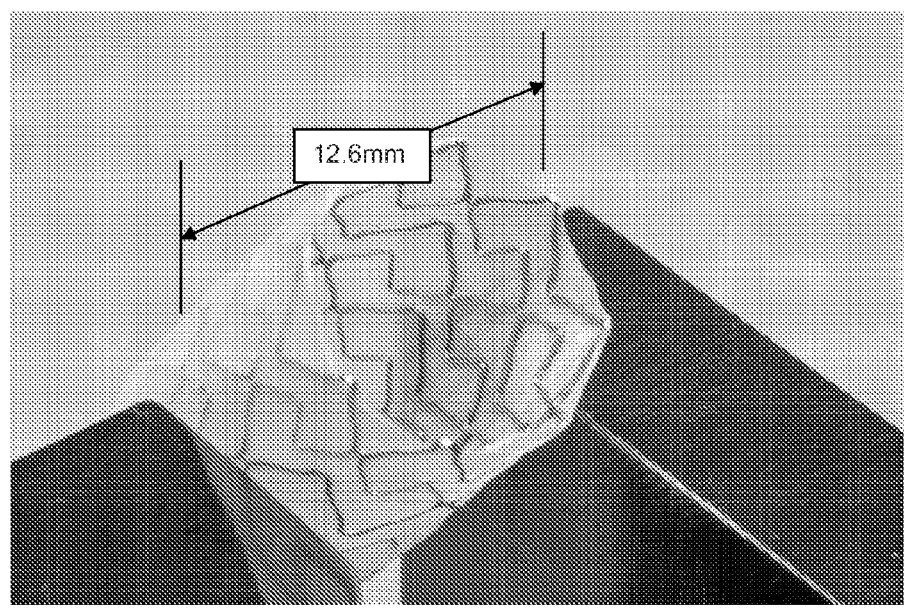
FIG. 3f is a photomicrograph showing the inside of a covered stent of the present invention that is fully deployed.

The present invention addresses the problem of wrinkles in the covers in stent-grafts. The covers of self-expanding stent-grafts heretofore exhibited wrinkles when deployed to diameters smaller than the diameter at which the cover was applied to the stent, which is typically the fully deployed diameter. Inasmuch as body conduits are rarely the exact diameter of the stent-graft, rarely uniformly circular in cross-section, and rarely non-tapered, sections or entire lengths of self-expanding stent-grafts frequently are not fully deployed and hence present wrinkled surfaces to flowing blood or other body fluids. Furthermore, covered stents are often intentionally implanted at less than their fully deployed diameters in order to utilize their inherent radial expansion force to better anchor the devices against the host tissue, thereby preventing device migration in response to blood flow. Such practices come at the expense of having to tolerate devices with at least partially wrinkled covers. The present invention involves the use of a unique stent cover material, one that combines two seemingly mutually exclusive properties—being both strong enough to withstand the forces exerted by constant, cyclic blood pressure and also distensible enough to expand in response to the expansion forces exerted by a self-expanding stent.

In addition, a unique manufacturing method had to be devised in order to utilize this material to construct a self-expanding stent-graft. The temperature-constrained shape-memory properties of self-expanding stents introduce significant processing challenges. Ultimately, a process was developed which entailed not only applying the cover to the stent in a cold environment, but also entailed bonding the cover to the stent at these cold temperatures.

Referring to FIGS. 1a and 1b, the present invention is directed to implantable device 60 having a self-expanding stent component 63 with either an inner or outer cover 62 (or both), that is wrinkle-free over an operating diametric range of the device. The cover 62 has wrinkles 65 in the constrained state as shown in FIG. 1a. The wrinkles disappear once the device self-expands to the diameter at which the cover was applied to the stent. The cover 62 remains wrinkle-free as the device 60 self-expands even further as shown in FIG. 1b. The invention addresses the clinical problems associated with wrinkles in self-expanding stent covers while providing the minimum amount of covering material. Wrinkles are known to disrupt blood flow and become sites for clot deposition which can ultimately lead to graft thrombosis and embolus shedding. These sequelae may create serious clinical consequences, especially in organs such as the brain. The incorporation of a single, very thin cover enables a stent-graft device with a profile dictated primarily by the stent strut dimensions, not by the mass or volume of the cover. The present invention, therefore, provides a heretofore unavailable combination of deployment diameter for a given size stent-graft and a wrinkle-free cover surface over a wide range of deployed diameters.

For use in the present invention, nitinol (nickel-titanium shape memory alloy) and stainless steel are preferred stent materials. Nitinol is preferred for its shape memory properties. The memory characteristics can be tailored for the requirements of the stenting application during the fabrication of the alloy. Furthermore, nitinol used to make the stent can be in the form of wire that can be braided or welded, for example, or it can be tubing stock from which a stent is cut. While nitinol offers a wide variety of stent design options, it should be appreciated that stainless steel and other materials may also be formed into many different shapes and constructs.

Stent covers of the present invention are preferably durable and biocompatible. They may be seamless or contain one or more seams. The stent covering of the present invention has a low Young's modulus, which enables it to be distended with the minimal force that is exerted by a self-expanding stent. Furthermore, the covering is provided with a minimal (or non-existent) elastic recoil force so that after stent expansion the covering does not cause the stent-graft to decrease in diameter over time. The cover is also preferably thin. Thinness has the multiple benefits of reducing the introduction size of the device, maximizing the blood flow cross-section, providing less resistance to radial expansion, and introducing less elastic recoil.

In a preferred embodiment, a nitinol stent is chilled and crushed to a diameter less than the fully deployed outer diameter. The chilling is desirable to help maintain the stent in the crushed state. The covering is then applied without creating wrinkles. The constrained diameter is selected according to the intended operating parameters of the device, such as about 90% of the fully deployed outer diameter or less, about 80% of the fully deployed outer diameter or less, about 70% of the fully deployed outer diameter or less, about 60% of the fully deployed outer diameter or less, and for most applications most preferably about 50% of the fully deployed outer diameter or less. While maintaining the device in the chilled state, the stent-graft is allowed to dry and then further crimped with a chilled crimping tool and transferred into a delivery catheter.

The stent cover may consist of fluorinated ethylene propylene (FEP) coating the nodes and fibrils of ePTFE film. Most preferably, a cover of ePTFE, is used to practice the invention. Whereas ePTFE is known for its high tensile strength, that strength is imparted only in the direction of expansion. If the ePTFE material is not expanded in the orthogonal direction (i.e., the transverse direction in the case of films) during the processing of the material, the ePTFE material is extremely distensible in that direction. Such materials have both very low tensile strength and very low Young's modulus in the transverse direction. The low Young's modulus property enables the material to distend under low forces. Films used to construct articles of the present invention can be easily elongated in the transverse direction by hand, thereby demonstrating their low Young's modulus values. In the most preferred embodiments, therefore, the ePTFE materials are in the form of very thin, highly porous films that are highly distensible in the transverse direction. The combination of high porosity and thinness result in a cover material that occupies minimal volume of the device. Expanded PTFE stent covers may offer additional advantages by virtue of the ability to provide and control their porosity. Various agents or fillers can be added to the surface or within the pores of the material. Such agents and fillers may include but are not limited to therapeutic drugs, antithrombotic agents, and radio opaque markers. If desired, portions of or the entire ePTFE cover may optionally be rendered non-porous or non-permeable by densifying, filling the pores, or through any other suitable means. Preferably, to provide added stability to the material, the ePTFE material is raised above its crystalline melt point, that is, the ePTFE material is "sintered."

It is believed that thin ePTFE films possessing a thickness of less than about 0.25 mm are preferred for practicing the present invention. It is believed that even more preferred are films possessing a thickness less than about 0.1 mm. Preferred thin ePTFE films possess densities in the range of about 0.2 to about 0.6 g/cc. It is believed that more preferred thin ePTFE films have densities in the range of about 0.3 to about 0.5 g/cc. It is believed that preferred thin ePTFE films possess matrix tensile strengths in the range of about 70 to about 550 MPa and about 15 to about 50 MPa, in the longitudinal and transverse directions, respectively. It is believed that more preferred thin ePTFE films possess matrix tensile strengths in the range of about 150 to about 400 MPa and about 20 to about 40 MPa, in the longitudinal and transverse directions, respectively. The preferred film for use in practicing the present invention is a thin ePTFE film possessing a thickness of about 0.02 mm, a density of about 0.4 g/cc, longitudinal matrix strength of about 260 MPA, and a transverse matrix tensile strength of about 30 MPa.

It is believed that preferred thin ePTFE films possess Young's modulus in the range of about 100 to about 500 MPa and about 0.5 to about 20 MPa, in the longitudinal and transverse directions, respectively. It is believed that more preferred thin ePTFE films possess Young's modulus in the range of about 200 to about 400 MPa and about 1 to about 10 MPa, in the longitudinal and transverse directions, respectively. The most preferred Young's modulus values of the film in the longitudinal and transverse directions are about 300 MPa and about 2 MPa, respectively. This film is exceedingly distensible in the transverse direction.

The choice of film properties is largely dependent on the force the self-expanding stent exerts on the material during expansion. For example, stronger films may be used with stents that exert higher radial forces during self-expansion.

To take advantage of the low Young's modulus of the film, the covered stent may be constructed with the low Young's modulus direction of the film oriented in the circumferential direction of the stent. The high strength direction of the film is therefore oriented in the axial direction of the stent. Preferably, the film is applied to the stent in the shape of a tube. A film tube is constructed by rolling multiple layers of the film around the circumference of a mandrel that is covered with a release material (such as Kapton film, part number T-188-1/1, Fralock Corporation, Canoga Park, Calif.). Preferably, three or fewer ePTFE film layers are applied, more preferably a single layer is applied wherein the overlap seam is narrow and comprises only two layers of the film.

The film tube can be attached to the stent by suturing, gluing, and the like. Gluing is preferred, utilizing an adhesive or combination of adhesives by means such as spraying or dipping. It is preferred to dip coat a fully deployed stent with an adhesive, ensuring that the adhesive does not span the openings in the stent. Thermal or ambient cured adhesives can be used. When bonding the film tube to a shape memory metal stent using a thermally-activated adhesive, the adhesive should be curable at a temperature below the critical transition temperatures of the metal. Adhesives such as perfluoroethylvinylether-tetrafluoroethylene (PEVE-TFE) or perfluoropropylvinylether-tetrafluoroethylene (PPVE-TFE) are preferred. Terpolymers containing at least two of the following monomers are also preferred: PEVE, PPVE, perfluoromethylvinylether (PMVE), and TFE. Most preferably, the adhesive is perfluoromethylvinylether-tetrafluoroethylene (PMVE-TFE) material when bonding the cover to a nitinol stent.

FIG. 2a depicts a cross-section of the covered stent of the present invention that was constructed at 50% of the fully deployed outer diameter, crimped and transferred inside a delivery catheter, and then deployed to 30% of the fully deployed outer diameter of the device. The stent cover 62 can be attached to the outer surface of the stent by bonding it to stent struts 68 as shown in FIG. 2a, thereby providing an outer stent cover 51 to the stent 63. The cover 62 can alternatively be bonded to the inner surface of the stent as shown in FIG. 4b, providing an inner stent cover 41.

The most preferred way to attach the film tube to the outer surface of the stent involves placing the film tube inside a rigid (e.g., glass) tube that has an inner diameter smaller than the fully deployed out diameter of the stent, then inserting the crimped stent inside the film tube and bonding the stent and film tube together.

The film tube covering is first inserted inside the constraining tube without creating wrinkles. The ends of the film tube may be everted over the ends of the constraining tube. Preferably the ends are everted to the extent that modest tension is applied to the film tube, enough to hold the film tube taut and thereby keep the film tube free of wrinkles. As has been noted, the inner diameter of the constraining tube, and hence the constraining diameter, should be less than the fully deployed diameter of the device, such as 90% of the fully deployed outer diameter or less, about 80% of the fully deployed outer diameter or less, about 70% of the fully deployed outer diameter or less, about 60% of the fully deployed outer diameter or less, or about 50% of the fully deployed outer diameter or less.

A nitinol stent is prepared by dip coating a thin layer of adhesive to its struts and allowing the adhesive to dry. The preferred adhesive is PMVE-TFE, such as that taught in Example 5 of US Patent Application 2004/0024448 to Chang et al. Contrary to practices in the prior art that teach bonding covers to stents at ambient or even highly elevated temperatures, the cover is applied to the stent at lower than ambient temperatures. Preferably, the stent is chilled and crimped in a cold chamber (e.g., the freezer compartment of a refrigerator). The low temperature process is desired in order to cool the stent in order to dimensionally stabilize it at a diameter less than the film tube diameter while the cover is attached. The crimped stent is next inserted inside the film tube, which is inside a rigid tube. The assembly is permitted to warm to ambient temperature. The stent expands, hence comes in intimate contact with the film tube, as it warms. The assembly is submerged in a solvent that activates the PMVE-TFE adhesive and then warmed above ambient temperature to evaporate the solvent, thus allowing the adhesive to solidify.

The device inside the rigid tube is then again chilled in a freezer to a temperature at which at the device does not self-expand if unconstrained and then the stent-graft is removed from the tube. At this point, the stent-graft is further crimped using the chilled crimping machine, and transferred inside of a delivery catheter. Instead of crimping at this stage, alternatively the porous ePTFE cover of the stent-graft device may be rendered non-permeable. One method to do so can be achieved by dipping the device into a chilled dilute solution of elastomeric material, such as PMVE-TFE, PEVE-TFE, PPVE-TFE, or silicone. A dilute solution is preferred inasmuch as the solution becomes significantly more viscous when chilled to the same temperature as the device. Once the solution dries, the stent-graft can be crimped further, as previously described, and transferred inside of a delivery catheter.

Therapeutic agents, fillers, or the like can be added to the stent cover, the adhesive used to bond the stent cover to the stent or the elastomer material used to render the cover non-permeable or any combination thereof.

Stent-grafts made in this manner exhibit wrinkle-free coverings over the device diameter range extending from the diameter at which the covering was applied up to and including the fully deployed diameter. FIG. 2b illustrates the wrinkle-free stent cover 62 (in this case, on the outer surface of the stent) at the diameter at which it was bonded to the stent struts 68, thereby forming the covered stent device 60. The thin cover 62 stretches and remains wrinkle free up to and including the fully deployed diameter as shown in FIG. 2c. FIG. 2c depicts a cross-section of the covered stent of FIG. 1b. In order to achieve this device performance, the covering should be applied to the stent at a diameter smaller than the fully deployed diameter. This diameter should be no larger than the smallest intended diameter of the implanted device. Crushing the device below the diameter at which the cover was applied induces wrinkles in the stent cover. For example, crushing a device of the present invention to such a degree that it is small enough to be transferred to inside a delivery catheter will induce wrinkles in the stent cover. The wrinkles are no longer present once the deployed stent-graft reaches the diameter at which the cover was applied. Attaching the covering at an intermediate stent size means less crushing is necessary to decrease the stent-graft diameter for insertion into the delivery catheter. The likelihood of perforating the cover during the crushing process is reduced when less crushing is needed.

A stent-graft with an inner cover can be fabricated with a film tube and an adhesive-coated stent as previously described. The stent can be chilled then crushed and constrained inside a constraining tube. The film tube can then be mounted onto a balloon, introduced inside the stent, pressed against the stent via inflating the underlying balloon, then bonded to the stent by immersing the assembly into the appropriate solvent for the adhesive, and then allowed to dry. The balloon is then deflated and the stent-graft plus the constraining tube are again chilled to enable removal of the constraining tube prior to further radial crushing of the stent-graft and loading the device into the delivery system.

The present invention also minimizes flow disturbances caused by blunt stent strut profiles. As seen in FIG. 2b and FIG. 2c the adhesive material 22 bonded to stent strut 68 forms a smooth gradual transition where it attaches to stent cover 62. In the absence of this transition, the stent strut 68 may present a blunt profile to the flowing blood.

The wrinkle-free feature of articles of the present invention can benefit the performance of tapered stent-grafts. Tapered grafts are widely used in the treatment of aortoiliac disease. The present invention, which can include or not include a tapered stent and/or cover, can be implanted inside a tapered vessel without exhibiting wrinkles in the cover. That is, regardless of the shape of the starting materials, the device of the present invention can conform to become a tapered self-expanding stent-graft when deployed within a tapered body conduit. This allows tapered body conduits to be treated with non-tapered devices that are easier and less expensive to construct, without deploying an improperly sized stent-grafts. This also allows for a wider range of effective deployable sizes and shapes without the need to increase the number of different configurations of products.

The present invention has particular value in very demanding, small caliber stenting applications. These are applications in which a cover is needed to either protect against plaque or other debris from entering the blood stream after balloon angioplasty or to seal an aneurysm. Perhaps the most demanding applications are those involving the treatment of carotid and neural vessels where even small wrinkles in the stent cover may create a nidus for thrombosis. Given the sensitivity of the brain, the consequences of such thrombus accumulation and possible embolization can be dire. Not only does the present invention overcome the challenging problem of providing a wrinkle-free cover in a viable stent-graft, it accomplishes this with a surprisingly minimal amount of covering material. It was unanticipated that such a distensible, thin, and low mass material could satisfactorily perform as a stent covering.

The following examples are intended to illustrate how the present invention may be made and used, but not to limit it to such examples. The full scope of the present invention is defined in the appended claims.

EXAMPLES

To evaluate the examples, the following test methods were employed.

Test Methods

Assessment of Wrinkles

Stent-graft device covers were visually examined without the aid of magnification at ambient temperatures. Microscopic examination might be warranted for very small devices. The ends of devices were secured within a hollow DELRIN® acetal resin block in order fix the longitudinal axis of the device at an angle of about 45° above horizontal which enabled viewing the inner surface of the stent-grafts. The devices were positioned to allow examination of free edge of the device and stent openings nearest the ends of the device. Stent-grafts that were not fully deployed were constrained inside rigid tubes during examination. Fully deployed devices were submerged in an about 37° C. water bath prior to examination.

Alternatively, optical or scanning electron microscopy could be used to look for the presence or absence of wrinkles.

Dimensional Measurements

Stent and covered stent device outer diameters were measured with the aid of a tapered mandrel. The end of a device was slipped over the mandrel until the end fit snuggly onto the mandrel. The outer diameter of the device was then measured with a set of calipers. Optionally, a profile projector could be used to measure the outer diameter of the device while so placed on the mandrel.

The fully deployed outer diameter was measured after allowing the self-expanding device to fully deploy in a 37° C. water bath for 30 seconds, then measuring the device diameter in the water bath in the manner previously described.

For devices constrained inside constraining means having a round cross-section, the device outer diameter in the constrained state was taken to be the inner diameter of the constraining means.

In order to examine a device at some percentage of the fully deployed diameter of the device, the fully deployed diameter must first be known. A length of a device can be severed from the entire device and its fully deployed diameter can be measured. For example, a length of the device can be released from the delivery catheter and its diameter measured after being fully deployed in a 37° C. water bath.

Tensile Break Load, Matrix Tensile Strength (MTS), and Young's Modulus Determinations Tensile break load of the film was measured using a tensile test machine (Model 5564, Instron Corporation, Norwood, Mass.) equipped with flat-faced grips and a 10 N and 100 N load cells for the transverse and longitudinal values, respectively. The gauge length was 1 inch (2.54 cm) and the crosshead speed was 1 in/min (2.54 cm/min). Each sample was weighed using a Mettler AE2000 scale (Mettler Instrument, Highstown, N.J.), then the thickness of the samples was measured using a snap gauge (Mitutoyo Absulute, Kawasaki, Japan). A total of ten samples were tested. Half were tested in the longitudinal direction, half were tested in the transverse (i.e., orthogonal to the longitudinal) direction and the average of the break load (i.e., the peak force) was calculated. The longitudinal and transverse MTS were calculated using the following equation:

$$MTS = (\text{break load/cross-section area}) * (\text{density of PTFE})/\text{bulk density of the film}),$$ wherein the density of PTFE is taken to be 2.2 g/cc.

Young's modulus was determined from tensile test data obtained using a tensile test machine (Model 5500, Instron Corporation, Norwood, Mass.). The test was performed using a sample gauge length of 1 inch (2.54 cm) and a cross-head speed of 1 in/min (2.54 cm/min). A total of ten samples were tested. Half were tested in the longitudinal direction, half were tested in the transverse (i.e., orthogonal to the longitudinal) direction.

Inventive Example 1

Figure 4A:
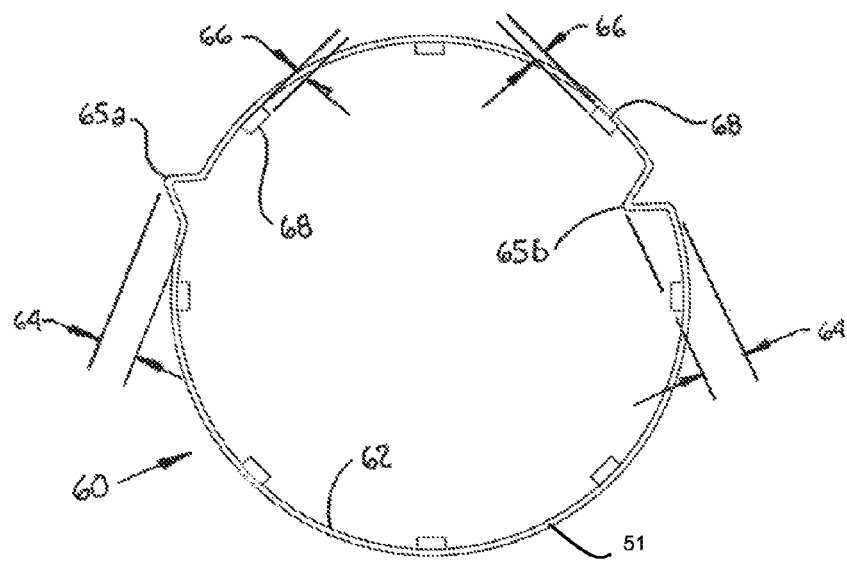
FIG. 4a is a transverse cross-section view of exemplary wrinkles in a cover on the outer surface of the stent.
Figure 4B:
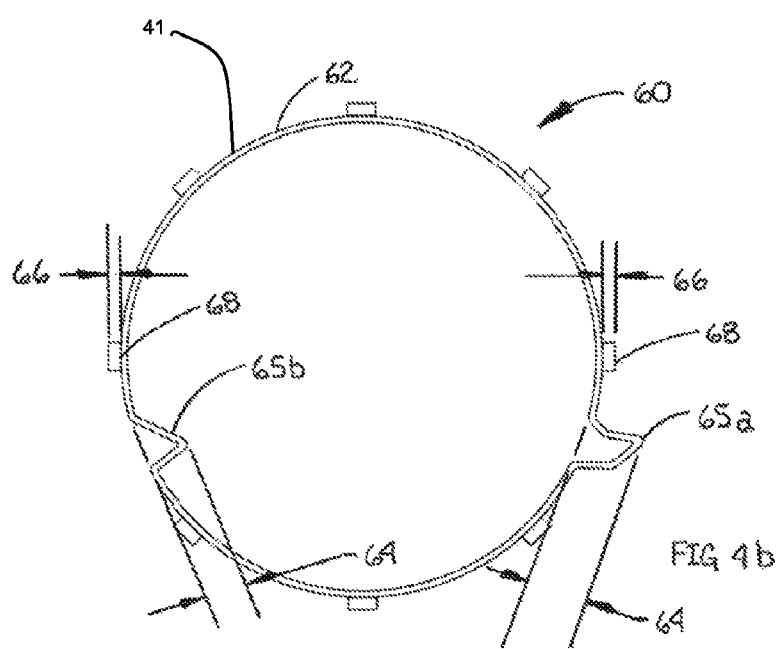
FIG. 4b is a transverse cross-section view of exemplary wrinkles in a cover on the inner surface of the stent.

Tubular, self-expanding nitinol stents constructed using the pattern as described in FIG. 4 of U.S. Pat. No. 6,709,453 to Pinchasik et al., were obtained. The stents had an outer diameter of approximately 8 mm and lengths of about 44 mm. Six sections about 15 mm in length were cut from the stents. Each of the six sections was processed in the following manner. The stent was dip-coated with PMVE-TFE, a liquefied thermoplastic fluoropolymer as described in Example 5 of US Patent Application 2004/0024,448 of Chang, et. al.

A short piece of silver-plated copper wire (approximately 0.5 mm in diameter) was fashioned into a hook and used to suspend the stent. The stent was submerged in a 3% by weight solution of PMVE-TFE and FC-77 solvent (3M Fluoroinert, 3M Specialty Chemicals Division, St Paul, Minn.). The dipped stent was removed from the solution and air-dried. The hook attached to the opposite end of the stent and the dipping process was repeated. The stent was next dipped in a 2% by weight solution of the fluoropolymer and the solvent, then air-dried. Once again, the hook was attached to the opposite end of the stent and the stent was again dipped into the 2% solution. This dipping process, therefore, consisted of four total dips, which yielded a uniform and uninterrupted layer of thermoplastic fluoropolymer on the stent struts. The amount of material applied weighed approximately 0.01 grams as determined by weighing the stent before and after the dipping process.

A stent covering was made as follows. A 4.0 mm stainless steel mandrel was obtained. A 4 mm inner diameter thin-walled (wall thickness of about 0.1 mm) ePTFE tube was fitted over the mandrel. The purpose of this tube was to later assist in removing the stent cover from the mandrel. Next, a spiral wrapping of ribbon of polyimide sheeting (KAPTON®, Part Number T-188-1/1, Fralock Corporation, Canoga Park, Calif.) was applied on top of the ePTFE tube to completely cover a 75 mm length of the graft.

A thin ePTFE film with the following properties was obtained: width of about 50 mm, matrix tensile strength in the longitudinal direction of about 256 MPa, matrix tensile strength in the transverse direction of about 31 MPa, a thickness of 0.02 mm, and a density of about 0.39 g/cc. (The tensile strengths in the longitudinal and transverse directions were 45 MPa and 5 MPa, respectively.) Young's modulus values of the film in the longitudinal and transverse directions were 282 MPa and 1.9 MPa, respectively. An approximately 80 mm length of the film was applied on top of the polyimide sheeting in the axial direction of the mandrel such that the ends of film were in direct contact with the thin-walled ePTFE tube. The corners of these ends were heat bonded to the thin-wall tube with the use of a local heat source (Weller Soldering Iron, model EC200M, Cooper Tools, Apex, N.C.) set to 343° C. With the film tacked in place in this manner, one layer of the film was wrapped about the circumference of the mandrel. Wrapping of the film was performed under minimal tension in order to avoid stretching the film. Approximately a 2 mm width of overlap region was created. The film layers in this overlap region were heat bonded together with the soldering iron set to 343° C. to form a seam. For this construction, therefore, the longitudinal direction of the film, which was its high strength direction, was oriented along the length of the mandrel. The weaker, transverse, film direction was oriented in the circumferential direction of the mandrel.

A second layer of polyimide film was helically wrapped on top of the ePTFE film, completely covering it. This entire assembly was then placed in a forced air oven (Model NT-1000, Grieve Corporation, Round Lake, Ill.) set at 370° C. The assembly was removed from the oven after 7 minutes and allowed to cool. After cooling, the outer wrap of polyimide film was removed. The film tube, inner layer of polyimide film, and the thin-walled ePTFE tube, together, were carefully removed from the mandrel. The thin-walled ePTFE tube was everted, thereby removing it from the polyimide film. The polyimide film was then carefully removed from the ePTFE film tube.

The stent and film tube were next assembled into a stent-graft. The ePTFE film tube was inserted inside a 60 mm long glass tube having an inner diameter of 4 mm and a wall thickness of 1 mm such that both ends of the film tube extended beyond the ends of the glass tube. The ends of closed forceps were then used to spread the ends of the film tube by placing them inside each end of the tube and then opening them. The film tube ends were everted over the outside of the glass tube. The film was tacky enough to secure the ends to the surface of the tube, thereby holding the wrinkle-free film tube in place. The glass tube with the ePTFE film tube inside it was placed in a conventional freezer set at approximately −15° C. Tools that would later be used to create the stent-graft, namely a set of tweezers and an iris-type stent crimping device, such as taught in US 2002/0138966 A1 to Motsenbocker, were also chilled in the freezer compartment.

The chilled crimping device was used to reduce the diameter of the adhesive-coated stent uniformly along its length. The outer diameter of the stent was reduced to about 3 mm. Using chilled tweezers, the following procedure was performed inside the freezer compartment. The stent was removed from the crimper and transferred into the ePTFE film tube that was inside the chilled glass tube. The glass tube, film tube and stent were then removed from the freezer and allowed to warm to ambient temperature. The stent, by virtue of its shape memory characteristics, self-expanded as the assembly warmed. In doing so, the stent exerted radial force against the film tube, creating intimate contact between the stent and the film-tube along the length of the stent.

Next, the stent cover was bonded to the stent. This assembly, still constrained by the 4 mm inner diameter of the glass tube, was then dipped in a container of FC-77 solvent for 40 seconds in order to activate the adhesive. The assembly was then allowed to dry for approximately 30 minutes while being warmed to 40° C. through the use of a halogen lamp. The assembly was allowed to cool to ambient temperature. In this way, a stent-graft device was created.

The stent-graft device was pushed to one end of the glass tube until the end of the stent was flush with the end of the glass tube. The ePTFE covering was trimmed flush with the stent. The process was repeated to trim the opposite end of the stent-graft. With the stent-graft still inside the glass tube, the device was inspected to ensure thorough and uniform bonding between the stent cover and the stent and to verify the absence of wrinkles in the covering.

The next step entailed loading the stent-graft into a delivery system. The stent-graft device, still constrained by the glass tube, was chilled in a freezer as previously described. The device was then transferred to inside a chilled iris crimper and further radially crushed to reduce its outer diameter to the desired delivery profile (i.e., crushed outer diameter), which was about 2 mm. The device was then transferred from the crimper into its intended delivery system. Thus, the device was prevented from self-expanding to its fully deployed outer diameter during the assembly and loading processes.

The resultant stent-graft device had a delivery profile of about 2 mm and a fully deployed outer diameter of 8 mm. Photographs were taken of the device at various stages of deployment and subsequent re-crushing. The outer diameter of the device was characterized as a percentage of the fully deployed outer diameter, which was about 8 mm. The fully deployed device outer diameter was about 8 mm at both about 37° C. and at ambient temperature. It should be noted that this may not be the case for other types of nitinol alloys.

FIGS. 3a through 3f are photomicrographs showing the inside of the six covered stents of this example. One device was transferred from its 2 mm delivery profile constraining sheath into a hollowed DELRIN® resin block with an inner diameter corresponding to about 50% of the fully deployed outer diameter of the device. This 50% of the fully deployed outer diameter corresponds to the outer diameter at which the device was made. Photomicrographs were taken of the end of the device as previously described. A representative image is shown as FIG. 3a. This photomicrograph indicates the absence of wrinkles in the stent covering. Another device was transferred into a hollowed DELRIN® resin block with an inner diameter corresponding to about 60% of the fully deployed outer diameter of the device. A representative image is shown as FIG. 3b. This photomicrograph indicates the absence of wrinkles in the stent covering. A third device was transferred into a hollowed DELRIN® resin block with an inner diameter corresponding to about 70% of the fully deployed outer diameter of the device. A representative image is shown as FIG. 3c. This photomicrograph indicates the absence of wrinkles in the stent covering. The fourth and fifth stent-grafts were transferred into hollowed DELRIN® resin blocks with inside diameters of 80% and 90% of the fully deployed outer diameter of the devices, respectively; representative photomicrographs appear in FIGS. 3d and 3e, respectively. The coverings were wrinkle-free in both of these states, as indicated in the photomicrographs. The sixth device was fully deployed in a 37° C. water bath and then examined under a microscope. A representative image is shown as FIG. 3f. This photomicrograph indicates the absence of wrinkles in the stent covering.

Comparative Example 2

Film used in the construction of the six stent-graft devices of Example 1 was used to make a stent-graft in accordance with the teachings of the prior art. The cover was applied to a length of a stent of the type previously-described. In this case, the cover was attached to the stent in the fully deployed state under ambient conditions. The cover was applied in the same manner as described previously. The stent-graft device was then transferred to inside a chilled iris crimper as previously described and further radially crushed to reduce its outer diameter to the desired delivery profile (i.e., crushed outer diameter), which was about 2 mm. The device was then transferred from the crimper into its intended delivery system. Thus, the device was prevented from self-expanding to its fully deployed outer diameter during the assembly and loading processes. The resultant stent-graft device had a delivery profile of about 2 mm and a fully deployed outer diameter of 8 mm. This device was deployed within a hollow DELRIN® resin cavity, as described in Example 1. The diameter of the hole in the block corresponded to about 50% of the fully deployed diameter of the device. A representative photomicrograph of the crushed device appears as FIG. 3g.

Figure 3G:
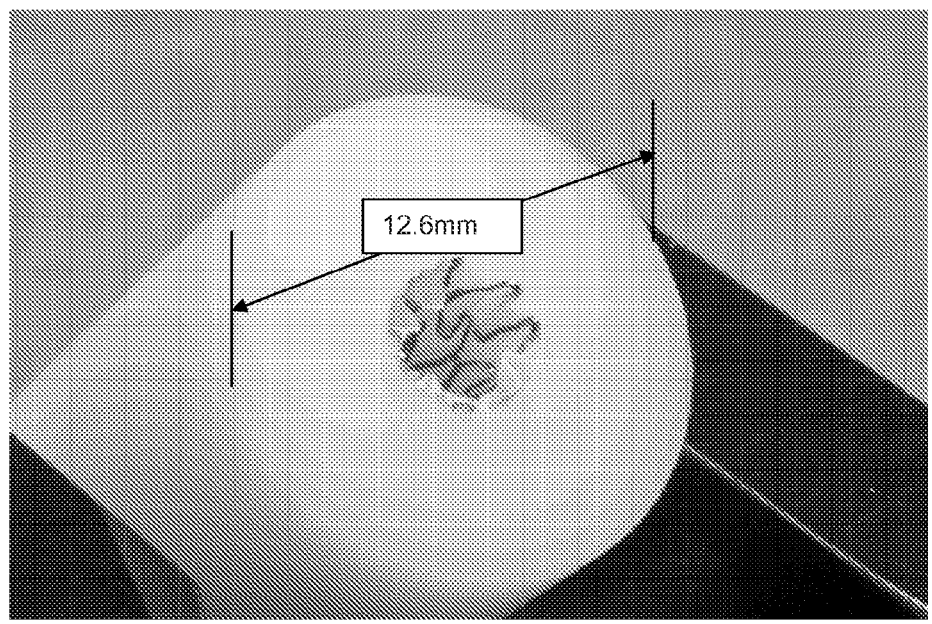
FIG. 3g is a photomicrograph showing the inside of a covered stent of the prior art that is constrained in a partially deployed state of about 50% of the fully deployed diameter.

The advantage of making the stent-graft device of the present invention in the above-described manner is clear when comparing FIG. 3a with FIG. 3g. Both photomicrographs were taken at 50% of the fully deployed outer diameter. FIG. 3a, unlike FIG. 3g, exhibits no wrinkles. FIG. 3a demonstrates the wrinkle-free benefit of the present invention. On the other hand, FIG. 3g demonstrates the wrinkles that result from crushing a film tube that was made at 100% of the deployed diameter, then crushed to 50% of the deployed diameter. Note the wrinkles in the leading edge of the cover in FIG. 3g.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A method of producing a stent-graft, comprising
   providing a stent;
   applying adhesive to the stent;
   chilling the stent;
   reducing the stent in diameter while chilled;
   providing a tubular cover;
   inserting the tubular cover into a tubular constraining device;
   chilling the cover and the tubular constraining device;
   inserting the stent that is chilled inside the cover that is chilled; and
   adhering the stent and cover together to create the stent-graft.

2. The method of claim 1, wherein providing a stent comprises providing a stent having shape memory characteristics.

3. The method of claim 2, wherein providing a stent having shape memory characteristics comprises providing a stent comprising nitinol.

4. The method of claim 2, further comprising adhering the stent and cover together at a temperature warmer than the temperature at which the stent was chilled.

5. The method of claim 1 further comprising compressing the stent-graft to a smaller diameter and placing into a delivery system.

6. The method of claim 4, wherein providing a tubular cover comprises:
   providing a tubular cover comprising an ePTFE film that possesses a density in a range of about 0.2 to about 0.6 g/cc, a matrix tensile strength in a range of about 70 to about 550 MPa in a longitudinal direction and in a range of about 15 to about 50 MPa in a transverse direction, and a Young's modulus in a range of about 100 to about 500 MPa in the longitudinal direction and in a range of about 0.5 to about 20 MPa in the transverse direction, wherein the longitudinal direction of the ePTFE film is substantially aligned with a longitudinal axis of the stent.

7. The method of claim 4, wherein providing a tubular cover comprises:
   providing a tubular cover comprising ePTFE film that possesses a density in a range of about 0.3 to about 0.5 g/cc.

8. The method of claim 4, wherein providing a tubular cover comprises:
   providing a tubular cover comprising ePTFE film that possesses a matrix tensile strength in a range of about 150 to about 400 MPa in a longitudinal direction and in a range of about 20 to about 40 MPa in a transverse direction.

9. The method of claim 4, wherein providing a tubular cover comprises:
   providing a tubular cover comprising ePTFE film that possesses a Young's modulus in a range of about 200 to about 400 MPa in a longitudinal direction and in a range of about 1 to about 10 MPa in a transverse direction.

10. The method of claim 4, wherein providing a tubular cover comprises:
    providing a tubular cover comprising ePTFE film that possesses a Young's modulus of about 300 MPa in a longitudinal direction and about 2 MPa in a transverse direction.

11. The method of claim 4, wherein providing a tubular cover comprises:
    providing a tubular cover comprising ePTFE film that possesses a thickness of about 0.02 mm, a density of about 0.4 g/cc, a longitudinal matrix strength of about 260 MPa, and a transverse matrix tensile strength of about 30 MPa.

12. A method of producing a stent-graft, comprising
    providing a stent having shape memory characteristics having a stent diameter at ambient temperature;
    applying adhesive to the stent;
    chilling the stent;
    reducing the stent in diameter while chilled to a diameter smaller than the diameter at ambient temperature;
    providing a tubular cover comprising ePTFE film having a cover diameter smaller than the stent diameter at ambient temperature;
    inserting the tubular cover into a tubular constraining device having an inner diameter smaller than the stent diameter at ambient temperature;
    chilling the cover and the tubular constraining device;
    disposing the stent that is chilled within the tubular cover that is chilled that is inside the tubular constraining device that is chilled;
    warming the tubular constraining device, the tubular cover and the stent to ambient temperature, wherein by virtue of its shape memory characteristics, the stent self-expands exerting radial force against the tubular cover creating intimate contact between the stent and the tubular cover along a length of the stent;
    bonding the tubular cover to the stent forming a stent-graft;
    chilling the stent-graft while remaining constrained by the tubular constraining device;

removing the stent-graft that is chilled from the tubular constraining device;

compressing the stent-graft that is chilled to a smaller diameter; and disposing the stent-graft that is chilled onto a delivery system.

13. The method of claim 12, wherein providing a tubular cover comprising ePTFE film comprises:

providing a tubular cover comprising an ePTFE film that possesses a density in a range of about 0.2 to about 0.6 g/cc, a matrix tensile strength in a range of about 70 to about 550 MPa in a longitudinal direction and in a range of about 15 to about 50 MPa in a transverse direction, and a Young's modulus in a range of about 100 to about 500 MPa in the longitudinal direction and in a range of about 0.5 to about 20 MPa in the transverse direction, wherein the longitudinal direction of the ePTFE film is substantially aligned with a longitudinal axis of the stent.

14. The method of claim 12, wherein providing a tubular cover comprising ePTFE film comprises:

providing a tubular cover comprising ePTFE film that possesses a density in a range of about 0.3 to about 0.5 g/cc.

15. The method of claim 12, wherein providing a tubular cover comprising ePTFE film comprises:

providing a tubular cover comprising ePTFE film that possesses a matrix tensile strength in a range of about 150 to about 400 MPa in a longitudinal direction and in a range of about 20 to about 40 MPa in a transverse direction.

16. The method of claim 12, wherein providing a tubular cover comprising ePTFE film comprises:

providing a tubular cover comprising ePTFE film that possesses a Young's modulus in a range of about 200 to about 400 MPa in a longitudinal direction and in a range of about 1 to about 10 MPa in a transverse direction.

17. The method of claim 12, wherein providing a tubular cover comprising ePTFE film comprises:

providing a tubular cover comprising ePTFE film that possesses a Young's modulus of about 300 MPa in a longitudinal direction and about 2 MPa in a transverse direction.

18. The method of claim 12, wherein providing a tubular cover comprising ePTFE film comprises:

providing a tubular cover comprising ePTFE film that possesses a thickness of about 0.02 mm, a density of about 0.4 g/cc, a longitudinal matrix strength of about 260 MPa, and a transverse matrix tensile strength of about 30 MPa.

19. The method of claim 12, wherein providing a stent having shape memory characteristics comprises providing a stent comprising nitinol.

* * * * *